United States Patent
Matsutani et al.

(10) Patent No.: US 9,623,186 B2
(45) Date of Patent: Apr. 18, 2017

(54) GASKET TO BE USED FOR MEDICAL SYRINGE, AND MEDICAL SYRINGE

(71) Applicant: SUMITOMO RUBBER INDUSTRIES, LTD., Kobe-shi, Hyogo (JP)

(72) Inventors: Yuichiro Matsutani, Kobe (JP); Naoyuki Ishida, Kobe (JP); Eiji Yao, Kobe (JP)

(73) Assignee: SUMITOMO RUBBER INDUSTRIES, LTD., Kobe-shi (JP)

( * ) Notice: Subject to any disclaimer, the term of this patent is extended or adjusted under 35 U.S.C. 154(b) by 0 days.

(21) Appl. No.: 14/729,921

(22) Filed: Jun. 3, 2015

(65) Prior Publication Data

US 2015/0367076 A1 Dec. 24, 2015

(30) Foreign Application Priority Data

Jun. 18, 2014 (JP) ................................. 2014-125210

(51) Int. Cl.
*A61M 5/315* (2006.01)
*F16J 15/00* (2006.01)

(52) U.S. Cl.
CPC .......... *A61M 5/31513* (2013.01); *F16J 15/00* (2013.01); *A61M 2205/0222* (2013.01); *A61M 2205/0238* (2013.01)

(58) Field of Classification Search
CPC .......... A61M 5/31513; A61M 5/31515; A61M 2005/31508; A61M 2005/3131; A61M 5/3129

USPC .......................................................... 604/221
See application file for complete search history.

(56) References Cited

U.S. PATENT DOCUMENTS

| | | | |
|---|---|---|---|
| 6,511,459 B1* | 1/2003 | Fago | A61M 5/31511 604/122 |
| 2010/0042055 A1 | 2/2010 | Sudo et al. | |
| 2013/0053786 A1* | 2/2013 | Maeda | B29C 33/42 604/187 |
| 2014/0228774 A1 | 8/2014 | Maeda et al. | |

FOREIGN PATENT DOCUMENTS

| | | |
|---|---|---|
| JP | 2892617 B2 | 5/1999 |
| WO | WO 2008/078467 A1 | 7/2008 |

* cited by examiner

*Primary Examiner* — Phillip Gray
(74) *Attorney, Agent, or Firm* — Birch, Stewart, Kolasch & Birch, LLP

(57) ABSTRACT

A gasket having a novel structure ensuring both the gas tightness and the low-friction slidability is provided. A sliding portion of the gasket (13) includes at least a first annular projection (17A), an annular recess and a second annular projection (17B) arranged in this order in a direction rearward from a distal portion of the gasket serving as a liquid contact portion. The first projection (17A) is designed so that a first peak appears adjacent the distal portion of the gasket when the gasket is fitted in the syringe barrel (11) and a product α of a contact pressure P1f and a width D1f of the first peak is 0.4≤α≤1.0 as determined by an FEM analysis.

2 Claims, 4 Drawing Sheets

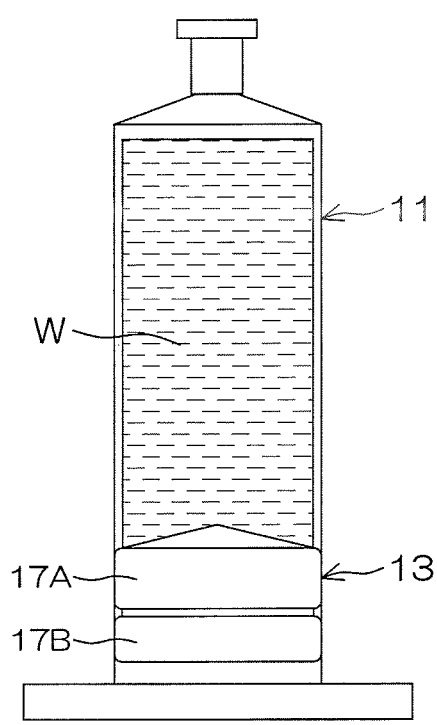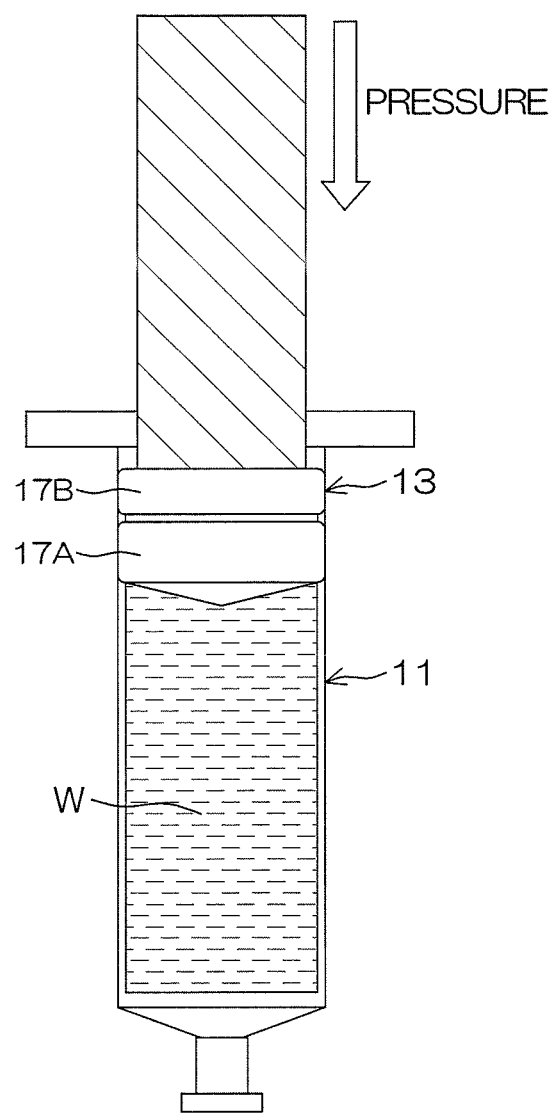

GASKET TO BE USED FOR MEDICAL SYRINGE, AND MEDICAL SYRINGE

CROSS-REFERENCE TO RELATED APPLICATION

This application corresponds to Japanese Patent Application No. 2014-125210 filed in the Japan Patent Office on Jun. 18, 2014, the disclosure of which is incorporated herein by reference in its entirety.

TECHNICAL FIELD

The present invention relates to a gasket to be used for a medical syringe, and a medical syringe.

BACKGROUND ART

Syringes for use in medical applications typically include a syringe barrel, a plunger reciprocally movable in the syringe barrel, and a gasket attached to a distal end of the plunger.

The gasket to be used for the syringes is required to have gas tightness and low-friction slidability. The gas tightness means that liquid drug is prevented from leaking outside during use and foreign matter is prevented from intruding from the outside. The low-friction slidability means that, when the syringe is used, a user can properly move the gasket by manipulating the plunger by one hand.

The prior-art syringes ensure the low-friction slidability and the gas tightness with a silicone oil applied in the syringe barrel, but some liquid drugs are adversely influenced by the silicone. Therefore, it is desirable not to apply the silicone to the syringe barrel.

From this viewpoint, a product called laminated gasket is often used, which includes a rubber gasket body having a surface laminated with a film having excellent slidability (e.g., a gasket laminated with a fluororesin film).

SUMMARY OF THE INVENTION

Problem to be Solved by the Invention

When the laminated gasket is inserted in the syringe barrel, a maximum diameter portion (peak portion) of the gasket receives a counter force from an inner surface of the syringe barrel to shrink and, therefore, a portion of the fluororesin film of the maximum diameter portion is liable to be wrinkled or slacked. At this time, a gap is formed between the wrinkled or slacked peak portion of the gasket and the inner surface of the syringe barrel. This may reduce the gas tightness of the gasket, thereby causing the liquid leakage and the intrusion of foreign matter.

In JP2892617B in the citation list, a distal portion of the gasket has a curvature radius R of not greater than 0.1 mm in peripheral section to increase the gas tightness, and a portion of the gasket opposite from a liquid contact portion has a reduced peripheral radius to improve the slidability.

If the distal portion of the gasket has an excessively small curvature radius R in peripheral section, however, the lamination film is more liable to be torn. Further, the gasket is more liable to be inclined in various steps of the gasket production process.

In WO2008/078467, on the other hand, the distal portion of the gasket has a curvature radius of not less than 0.7 mm in peripheral section, so that the gas tightness can be ensured even if the gasket is inclined. If the distal portion has an increased curvature radius R in peripheral section, however, the slidability is improved but the gas tightness is disadvantageously reduced.

In view of the foregoing, it is a principal object of the present invention to provide a gasket having a novel structure ensuring both the gas tightness and the low-friction slidability required for the gasket.

It is another object of the present invention to provide a medical syringe employing the gasket.

Solution to Problem

According to an inventive aspect of a first embodiment, there is provided a gasket to be used for a medial syringe, the gasket including: a rubber body having a liquid contact portion and a sliding portion to be brought into contact with an inner surface of a syringe barrel; and a lamination film provided on a surface of the rubber body; wherein the sliding portion includes at least a first annular projection, an annular recess and a second annular projection arranged in this order in a direction rearward from a distal portion of the gasket serving as the liquid contact portion; wherein the first projection is designed so that a first peak appears adjacent the distal portion of the gasket when the gasket is fitted in the syringe barrel and a product $\alpha$ of a contact pressure $P1f$ and a width $D1f$ of the first peak is $0.4 \leq \alpha \leq 1.0$ as determined by an FEM analysis.

According to an inventive aspect of a second embodiment, the lamination film is made of PTFE in the gasket of the first embodiment.

According to an inventive aspect of a third embodiment, two peaks including a distal peak and a rear side peak appear on the first projection of the gasket of the first embodiment.

According to an inventive aspect of a fourth embodiment, a product $\beta$ of a contact pressure P2 and a width D2 for the second projection of the gasket of the first embodiment is $0.2 \leq \beta \leq 0.6$ as determined by the FEM analysis.

According to an inventive aspect of a fifth embodiment, an edge portion of the first projection adjacent to the distal portion has a curvature radius of not greater than 1.2 mm in the gasket of the first embodiment.

According to an inventive aspect of a sixth embodiment, there is provided a medical syringe, which includes a tubular syringe barrel, a plunger combined with the syringe barrel and movable in the syringe barrel, and a gasket of the first embodiment attached to a distal end of the plunger.

In the conception of the present invention, it was found that the gas tightness and the low-friction slidability required for the gasket are related with the contact pressure at which the gasket presses the syringe barrel. That is, when an FEM (finite element method) analysis was performed with the gasket inserted in the syringe barrel, it was found that the gas tightness and the low-friction slidability were influenced by the contact pressure at which the gasket presses the syringe barrel.

Further, it was found that the gas tightness is significantly influenced by the contact pressure of the projection (first projection) adjacent to the distal portion of the gasket. Particularly, it was found that the product of the contact pressure ($P1f$) and the width (axial width $D1f$) of the peak appearing on the distal side of the first projection is a very important factor for the gas tightness.

It was confirmed that the gas tightness is impaired if the product of the contact pressure and the width is excessively small, and the slidability is impaired if the product is excessively great.

Further, it was confirmed that the sliding portion preferably includes the first projection as well as the annular second projection arranged in this order in the direction rearward from the distal portion for smooth sliding and capping.

It was also confirmed that the slidability is impaired if the product of the contact pressure (P2) and the axial width (D2) for the second projection is excessively great, and the gasket is liable to suffer from inconveniences, e.g., the gasket is liable to be obliquely inclined or permit intrusion of outside air, if the product is excessively small.

Further, it was found that the first projection is desirably configured so as to have a double-peak contact pressure profile as determined by the FEM analysis. Where the first projection has the double-peak contact pressure profile, the gasket has an improved gas tightness and, in addition, the gas tightness can be ensured even if the gasket is inclined during the handling.

Effects of the Invention

According to the present invention, the gasket has an improved gas tightness and, hence, improves the liquid drug storage stability when being used for a prefilled syringe.

Since the gasket slidability is not reduced, a user can use the syringe with a reduced load.

Further, the gas tightness and the slidability of the gasket can be estimated by the FEM analysis in the gasket production process, so that a safer gasket can be designed in a shorter period of time.

BRIEF DESCRIPTION OF THE DRAWINGS

FIGS. 4(A) and 4(B) are diagrams for explaining a gas tightness test and a slidability test.

EMBODIMENT OF THE INVENTION

With reference to the attached drawings, one embodiment of the present invention will hereinafter be described specifically.

Figure 1:
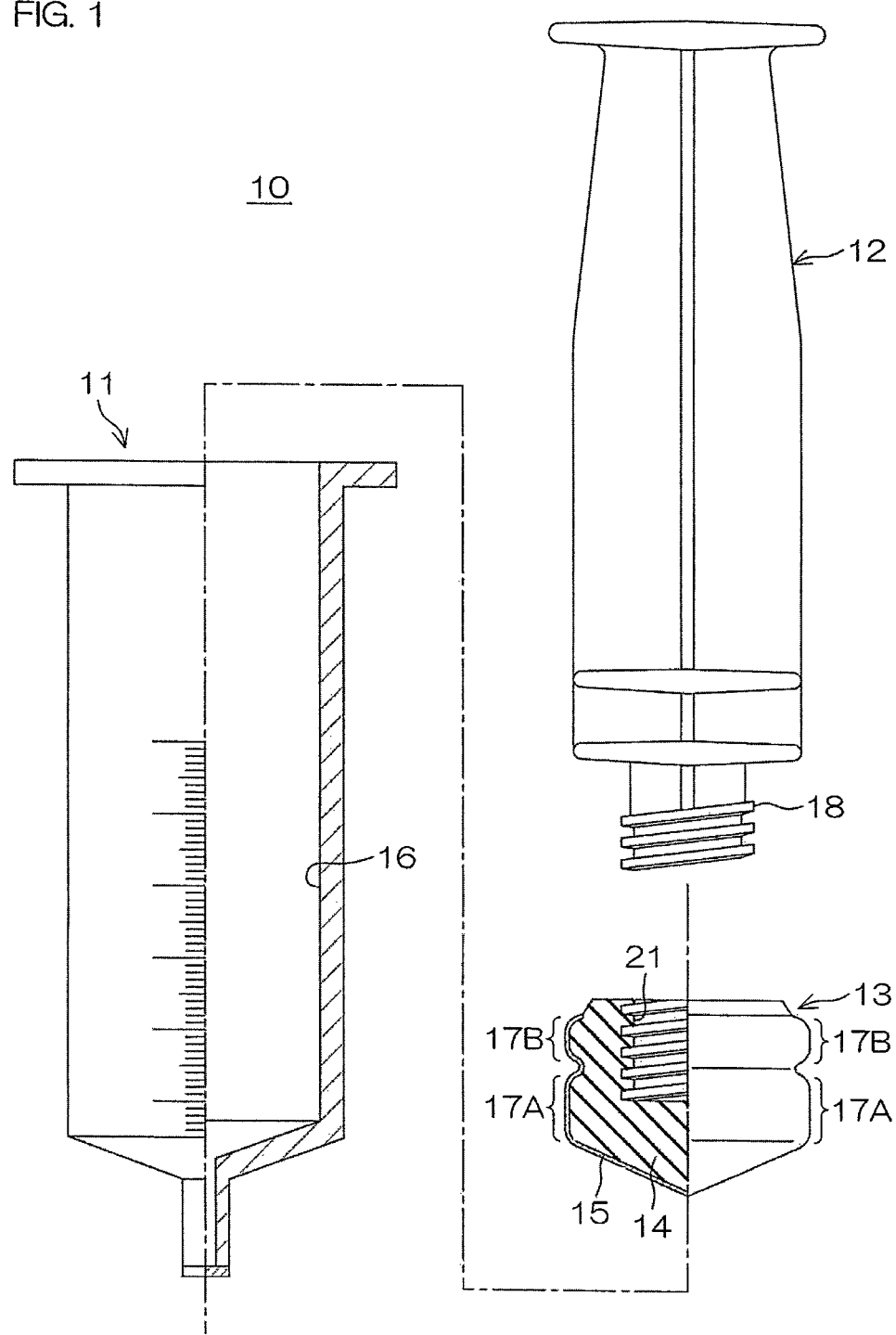
FIG. 1 is an exploded diagram illustrating a medical syringe according to an embodiment of the present invention.

FIG. 1 is an exploded diagram illustrating a medical syringe, i.e., a so-called prefilled syringe, according to the embodiment of the present invention. In FIG. 1, a half of a syringe barrel 11 and a half of a gasket 13 are illustrated in section.

Referring to FIG. 1, the prefilled syringe 10 includes a hollow cylindrical syringe barrel 11, a plunger 12 combined with the syringe barrel 11 and reciprocally movable in the syringe barrel 11, and a gasket 13 attached to a distal end of the plunger 12. The gasket 13 is a so-called laminated gasket, which includes a main body 14 made of an elastic material (a rubber or an elastomer) and a lamination film 15 provided on a surface of the main body 14. The gasket 13 includes two circumferential portions, i.e., a first projection 17A and a second projection 17B, serving as a sliding portion to be kept in gas-tight and liquid-tight contact with an inner peripheral surface 16 of the syringe barrel 11.

The plunger 12 includes a resin plate piece, for example, having a cross shape as seen in section, and a head 18 provided at a distal end of the resin plate piece and fitted with the gasket 13. The head 18 is an integral part of the plunger 12 made of a resin and shaped in a male screw.

The gasket 13 has a generally cylindrical shape having a short axis. The gasket 13 has a distal end face, for example, having a conical center portion projecting at an obtuse angle, and a rear end face axially recessed into an engagement recess 21 shaped in a female screw. The head 18 of the plunger 12 is screwed into the engagement recess 21 of the gasket 13, whereby the gasket 13 is attached to the distal end of the plunger 12.

Figure 2:
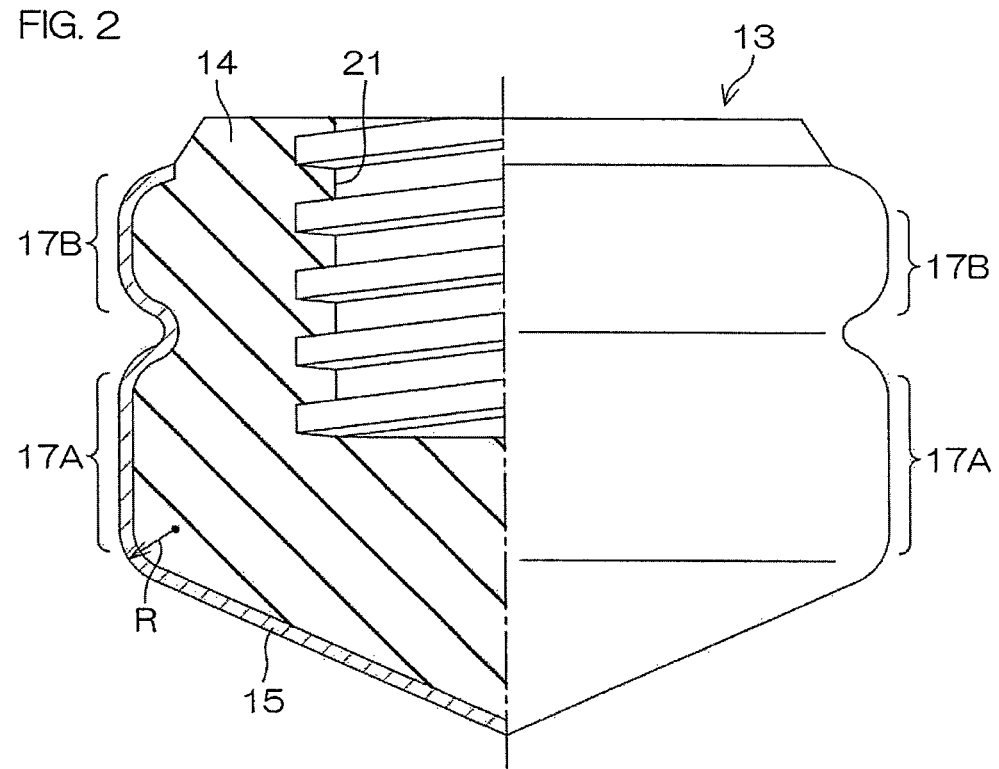
FIG. 2 is a diagram of a laminated gasket according to the embodiment of the present invention with a half of the gasket illustrated in section.

FIG. 2 is a diagram showing only the gasket 13 of FIG. 1 on an enlarged scale. In FIG. 2, a half of the gasket 13 is illustrated in section.

Referring to FIG. 2, the structure of the gasket 13 according to this embodiment will be described in greater detail.

The gasket 13 includes the main body 14, and the lamination film 15 provided on the surface of the main body 14. The main body 14 is made of an elastomeric rubber (crosslinked rubber).

The type of the lamination film 15 provided on the surface of the main body 14 is not particularly limited, as long as the lamination film 15 can prevent migration of components from the crosslinked rubber (main body 14) and is more excellent in slidability than the rubber, i.e., has a smaller friction coefficient than the rubber.

Exemplary materials for the main body 14 and the lamination film 15 are shown below.

<Rubber>

Examples of the rubber to be used as the material for the main body 14 include butyl rubbers, isoprene rubbers, butadiene rubbers, styrene-butadiene rubbers, natural rubbers, chloroprene rubbers, nitrile rubbers such as acrylonitrile-butadiene rubbers, hydrogenated nitrile rubbers, norbornene rubbers, ethylene-propylene rubbers, ethylene-propylene-diene rubbers, acryl rubbers, ethylene-acrylate rubbers, fluororubbers, chlorosulfonated polyethylene rubbers, epichlorohydrin rubbers, silicone rubbers, urethane rubbers, polysulfide rubbers, phosphazene rubbers and 1,2-polybutadiene rubbers.

These rubbers may be used either alone or in combination.

The rubber to be used for the main body 14 is not limited to the aforementioned rubbers, but is preferably a butyl rubber and/or an ethylene-propylene-diene rubber (hereinafter referred to as EPDM rubber).

The butyl rubber is preferred because of its excellent gas permeation resistance and water vapor permeation resistance.

A known butyl rubber compound may be used as the butyl rubber, but other examples of the butyl rubber include isobutylene-isoprene copolymer rubbers, halogenated isobutylene-isoprene copolymer rubbers (hereinafter referred to as halogenated butyl rubbers), and modification products of any of these rubbers. Examples of the modification products include bromination products of copolymers of isobutylene and p-methylstyrene. Particularly, the halogenated butyl rubbers are more preferred, and chlorinated butyl rubbers and brominated butyl rubbers are further more preferred for easy crosslinking.

The EPDM rubber is preferred because of its excellent processability. The EPDM rubber includes a non-oil extension type EPDM rubber containing only a rubber component and an oil extension type EPDM rubber containing a rubber component and an extension oil. In the present invention, either type of the EPDM rubbers may be used. Examples of a diene monomer for the EPDM rubber include dicyclopentadiene, methylene norbornene, ethylidene norbornene, 1,4-hexadiene and cyclooctadiene.

The halogenated butyl rubber and the EPDM rubber are advantageously used in combination because the resulting rubber is excellent in gas permeation resistance, water vapor permeation resistance and processability.

In this embodiment, the main body 14 is of the syringe gasket as a medical rubber product and, therefore, a butyl rubber having a lower gas permeability is preferably used as a principal rubber component. A triazine derivative crosslinking agent is preferably used as a crosslinking agent for cleanliness.

<Lamination Film 15>

The lamination film 15 is not particularly limited, but may be an inert film. At least one fluororesin selected from the group consisting of a polytetrafluoroethylene (PTFE), a modified polytetrafluoroethylene (modified PTFE, which is a copolymer of a 4F-monomer and a very small amount of a perfluoroalkoxide), a tetrafluoroethylene ethylene copolymer (ETFE), a tetrafluoroethylene perfluoroalkyl vinyl ether copolymer (PFA) and a polychlorotetrafluoroethylene (PCTFE), and/or an olefin resin are preferred for the lamination film 15 to provide excellent chemical resistance.

<Formation of Laminated Gasket 13>

The laminated gasket 13 according to this embodiment is produced by kneading ingredients blended in a predetermined blend radio by means of a sealed kneader, an open roll kneader or the like, forming the resulting kneaded product into an unvulcanized rubber sheet by means of a calendar or a sheet forming machine, placing the unvulcanized rubber sheet and the inert film each having a predetermined weight and size in superposition in a die, and press-forming the unvulcanized rubber sheet and the inert film into a laminated gasket sheet by means of a vacuum press.

Conditions for the forming are not particularly limited, but may be properly determined. The forming temperature is preferably 155° C. to 200° C., more preferably 165° C. to 180° C. The forming period is preferably 1 to 20 minutes, more preferably 3 to 15 minutes, further more preferably 5 to 10 minutes. The die to be used for the forming preferably has a sliding surface forming portion having a smooth die surface mirror-finished so as to have an arithmetic average roughness Ra of not greater than 0.03 μm as measured with a cutoff value of 0.08 mm. With the use of this die, the laminated rubber member thus formed can have a surface roughness smaller than the original surface roughness of the inert film. The arithmetic average roughness Ra is preferably not greater than 0.02 μm, more preferably not greater than 0.015 μm.

Thereafter, an unnecessary portion is cut away and removed from the formed gasket sheet. Then, the resulting product is cleaned, sterilized and dried, and then visually inspected. Thus, a primary gasket product is produced.

A feature of the gasket 13 according to this embodiment is that the gasket 13 includes the first projection 17A and the second projection 17B serving as the sliding portion to be kept in gas-tight and liquid-tight contact with the inner peripheral surface 16 of the syringe barrel 11, and that the first projection 17A is designed so that a product of a contact pressure P1$f$ and a width D1$f$ is $0.4 \leq \alpha \leq 1.0$ as determined by an FEM analysis.

More specifically, the first projection 17A is designed so that two peaks including a distal peak and a rear side peak appear and a product of a contact pressure P1$f$ and a width D1$f$ of the distal peak is $0.4 \leq \alpha \leq 1.0$.

Further, the first projection 17A has a distal edge portion having a curvature radius R of not greater than 1.2 mm.

With this design, the gasket 13 of this embodiment ensures the gas tightness and the low-friction slidability.

EXAMPLES

An FEM (Finite Element Method) analysis was performed on gaskets each having a shape as shown in FIG. 2, i.e., gaskets each having a sliding portion including a first projection 17A and a second projection 17B to be brought into contact with an inner peripheral surface 16 of a syringe barrel 11. A static implicit method was used for the analysis, and marc & mentat was used as an analysis software.

For production of the gaskets to be subjected to the analysis, main bodies 14 were each made of a rubber having a hardness of 60, and lamination films 15 were each made of a PTFE (having a tensile elasticity of 485 MPa and a Poisson's ratio of 0.46).

Figure 3:
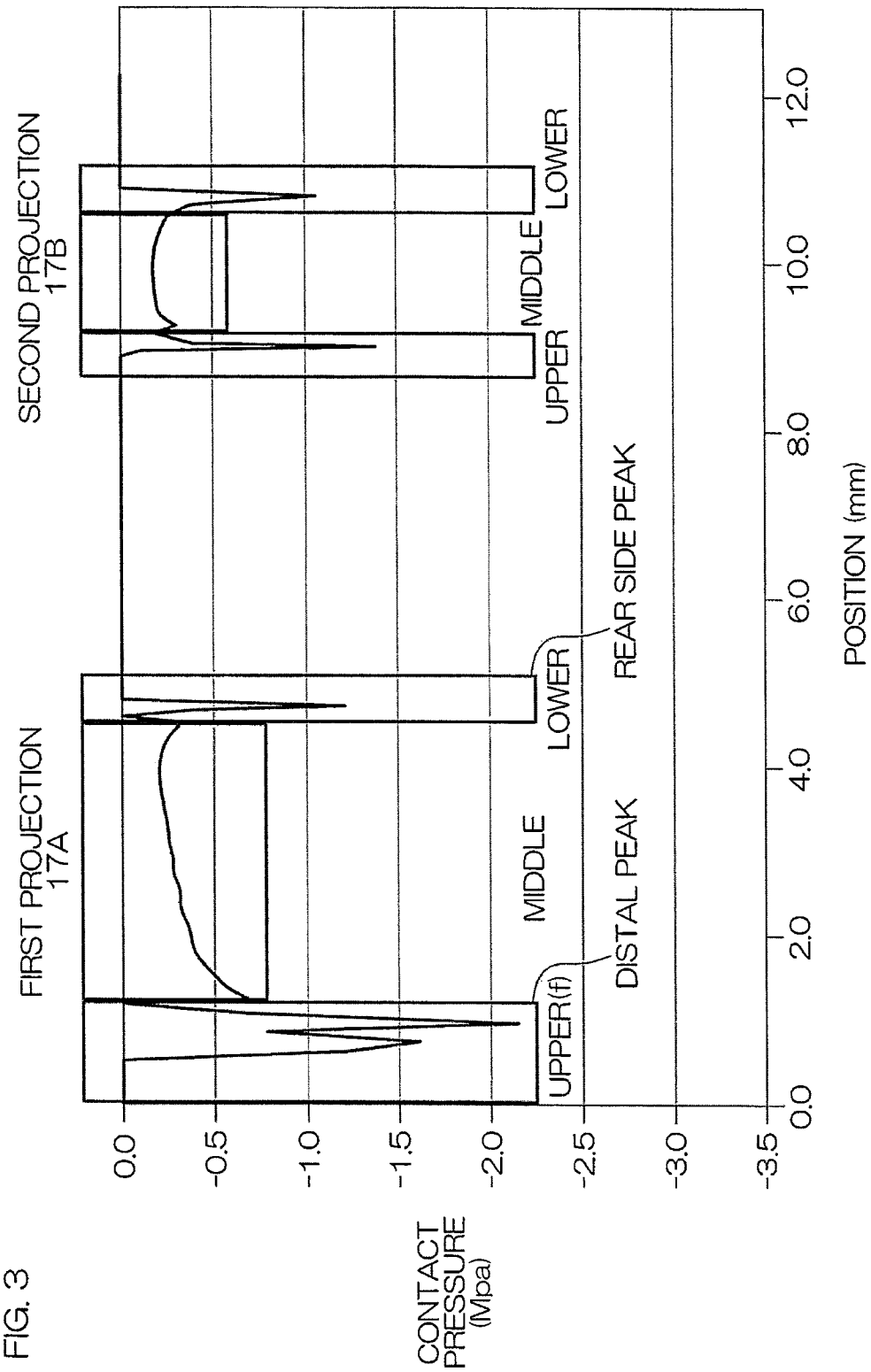
FIG. 3 is a diagram showing positions subjected to the FEM analysis.

For the first projection 17A of the gasket 13 fitted in the syringe barrel 11, a product α of a contact pressure P1$f$ and a width D1$f$ of a distal peak appearing at an analysis position in a contact pressure profile as shown in FIG. 3 was calculated.

Further, a product β of a contact pressure P2 and a width D2 of a peak observed at the second projection 17B by the FEM analysis was also calculated.

Further, a gas tightness test was performed as shown in FIGS. 4(A) and 4(B).

As shown in FIG. 4(A), the syringe barrel 11 was filled with pure water W, then capped with the gasket 13, and allowed to stand still.

As described above, the pure water was used as a test liquid, and COP's 100-mL syringe barrel was used as the syringe barrel 11. The capped syringe barrel was allowed to stand still at a temperature of 40° C. for 1 week.

The gasket 13 was observed to check whether the test liquid intruded over the first projection 17A located on the distal side (upper side in FIG. 4(A)) of the gasket 13 to reach the recess between the first projection 17A and the second projection 17B. Based on the observation results, where no liquid was present in the recess of the gasket, the gasket was rated as excellent (○). Where a small liquid droplet (having a size of not greater than 1 mm) was present in the recess of the gasket, the gasket was rated as acceptable (Δ). Where a large liquid droplet (having a size of greater than 1 mm) was present in the recess of the gasket, the gasket was rated as unacceptable (×).

Further, a slidability test was performed at a room temperature by sliding the gasket at a test speed of 5 mm/s by means of an autograph (available from Shimadzu Corporation) as shown in FIG. 4(B).

The gasket was evaluated based on a press load required for sliding the gasket. A gasket requiring a maximum load of not greater than 40 N was rated as acceptable (○), and a gasket requiring a maximum load of greater than 40 N was rated as unacceptable (×).

The results are collectively shown below in Table 1.

TABLE 1

|  | Comparative Example 1 | Comparative Example 2 | Example 1 | Example 2 | Example 3 | Example 4 | Example 5 |
|---|---|---|---|---|---|---|---|
| Curvature radius R of distal edge portion of first projection | 1.5 | 0.7 | 1 | 0.85 | 1.2 | 0.75 | 0.75 |
| First projection | | | | | | | |
| Diameter | 33.2 | 33.3 | 33.3 | 33.3 | 33.2 | 33.3 | 33.2 |
| Width | 3.2 | 3.6 | 3.9 | 3.6 | 3.2 | 3.9 | 3.6 |
| Second projection | | | | | | | |
| Diameter | 33.4 | 33.6 | 33.6 | 33.5 | 33.6 | 33.6 | 33.6 |
| Width | 1.2 | 1.7 | 1.7 | 1.7 | 1.7 | 1.7 | 1.7 |
| P1f · D1f (α) | 0.22 | 1.1 | 0.52 | 0.75 | 0.41 | 0.98 | 0.99 |
| P2 · D2 (β) | 0.36 | 0.54 | 0.57 | 0.54 | 0.52 | 0.51 | 0.52 |
| Gas tightness | x | ○ | ○ | ○ | Δ | ○ | ○ |
| Slidability | ○ | x | ○ | ○ | ○ | ○ | ○ | x: Unacceptable
Δ, ○: Acceptable

As can be understood from Table 1, the gasket is excellent in gas tightness and slidability, if the product α of the contact pressure P1f and the width D1f of the first peak appearing on the distal side of the first projection 17A is $0.4 \leq \alpha \leq 1.0$.

The results for Comparative Example 2 indicate that, if the product α of the contact pressure P1f and the width D1f of the first peak of the first projection 17A falls outside the aforementioned range, i.e., the product α is greater than 1.0, the slidability is impaired.

If the distal edge portion of the first projection 17A has a curvature radius R of not greater than 1.2 mm, i.e., the distal edge portion of the first projection 17A has a greater curvature radius R (e.g., has a chamfered surface), the gas tightness is poorer (see Comparative Example 1).

The present invention is not limited to the embodiment and the inventive examples described above, but various modifications may be made within the scope of the present invention.

What is claimed is:

1. A medical syringe comprising:
    a tubular syringe barrel;
    a plunger combined with the syringe barrel and movable in the syringe barrel; and
    a gasket attached to a distal end of the plunger, the gasket comprising:
    a rubber body having a liquid contact portion and a sliding portion to be brought into contact with an inner surface of the tubular syringe barrel; and
    a lamination film provided on a surface of the rubber body;
    wherein the sliding portion includes at least a first annular projection, an annular recess and a second annular projection arranged in this order in a direction rearward from a distal portion of the gasket serving as the liquid contact portion;
    wherein a diameter of the first annular projection is smaller than a diameter of the second annular projection;
    wherein the first projection is designed so that a distal peak appears adjacent the distal portion of the gasket when the gasket is fitted in the syringe barrel and a product α of a contact pressure P1f and a width D1f of the distal peak is $0.4 \leq \alpha \leq 1.0$ as determined by an FEM analysis;
    wherein a product β of a contact pressure P2 and a width D2 for the second projection of the gasket is $0.2 \leq \beta \leq 0.6$ as determined by an FEM analysis;
    wherein an edge portion of the first projection adjacent to the distal portion has a curvature radius of not greater than 1.2 mm, and
    wherein the lamination film is made of PTFE.

2. The gasket according to claim 1, wherein two peaks including the distal peak and a rear side peak appear on the first projection.

* * * * *

UNITED STATES PATENT AND TRADEMARK OFFICE
CERTIFICATE OF CORRECTION

PATENT NO.       : 9,623,186 B2
APPLICATION NO.  : 14/729921
DATED            : April 18, 2017
INVENTOR(S)      : Yuichiro Matsutani et al.

Page 1 of 1

It is certified that error appears in the above-identified patent and that said Letters Patent is hereby corrected as shown below:

In the Claims

In Claim 1, at Column 8, Line 33, change "product a" to read --product α--.

Signed and Sealed this
First Day of August, 2017

Joseph Matal
*Performing the Functions and Duties of the
Under Secretary of Commerce for Intellectual Property and
Director of the United States Patent and Trademark Office*